(12) United States Patent
Hardin, Jr.

(10) Patent No.: US 8,167,822 B2
(45) Date of Patent: May 1, 2012

(54) SPLITTABLE WIRE GUIDE

(75) Inventor: David M. Hardin, Jr., Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 515 days.

(21) Appl. No.: 11/960,190

(22) Filed: Dec. 19, 2007

(65) Prior Publication Data

US 2008/0154207 A1 Jun. 26, 2008

Related U.S. Application Data

(60) Provisional application No. 60/876,730, filed on Dec. 22, 2006.

(51) Int. Cl.
*A61M 25/00* (2006.01)

(52) U.S. Cl. .................................................. 600/585

(58) Field of Classification Search ................ 600/433, 600/434, 585; 604/164.13
See application file for complete search history.

(56) References Cited

U.S. PATENT DOCUMENTS

| | | |
|---|---|---|
| 4,824,435 A | 4/1989 | Giesy et al. |
| 5,046,497 A | 9/1991 | Millar |
| 5,513,650 A | 5/1996 | Johansen |
| 5,624,430 A | 4/1997 | Eton |
| 5,853,375 A | 12/1998 | Orr |
| 6,095,990 A | 8/2000 | Parodi |
| 6,497,670 B1 | 12/2002 | Parodi |
| 6,569,151 B1 | 5/2003 | Nash |
| 2002/0032432 A1 | 3/2002 | Nash et al. |
| 2002/0133092 A1 | 9/2002 | Oslund et al. |
| 2003/0120213 A1 | 6/2003 | Nash |
| 2003/0208220 A1* | 11/2003 | Worley et al. ............ 606/190 |
| 2004/0199088 A1* | 10/2004 | Bakos et al. ............. 600/585 |
| 2004/0220473 A1 | 11/2004 | Lualdi |
| 2005/0107737 A1* | 5/2005 | McDaniel ............. 604/95.04 |
| 2005/0261674 A1* | 11/2005 | Nobis et al. .............. 606/45 |

FOREIGN PATENT DOCUMENTS

| | | |
|---|---|---|
| DE | 38 02 976 C1 | 8/1989 |
| DE | 100 17 147 A1 | 10/2001 |
| EP | 1 240 915 A2 | 9/2002 |
| WO | WO 99/04725 | 2/1999 |
| WO | WO 00/12166 | 3/2000 |
| WO | WO 01/68177 A1 | 9/2001 |
| WO | WO 2005/021062 A2 | 3/2005 |

* cited by examiner

*Primary Examiner* — Max Hindenburg
*Assistant Examiner* — Jonathan M Foreman
(74) *Attorney, Agent, or Firm* — Brinks Hofer Gilson & Lione (57) ABSTRACT

A splittable wire guide having a plurality of separable elongate components that may be separated or otherwise re-positioned relative to each other so as to alter the physical properties of the wire guide or to form a plurality of separate wire guide members.

22 Claims, 6 Drawing Sheets

SPLITTABLE WIRE GUIDE

CROSS-REFERENCE TO RELATED APPLICATIONS

This application claims the benefit of U.S. Provisional Application Ser. No. 60/876,730, filed Dec. 22, 2006, entitled "Splittable Wire Guide", the entire contents of which are incorporated herein by reference.

TECHNICAL FIELD

The present invention relates to a wire guide for use in medical procedures and, in particular, to a wire guide that can be separated into two or more separate wire guide members.

BACKGROUND OF THE INVENTION

Wire guides are used in a variety of medical procedures. For example, wire guides are typically used to gain access into a blood vessel, duct, or organ during a minimally invasive medical procedure. Once the wire guide has been introduced and positioned, the wire guide may then be used to facilitate the subsequent introduction or placement of catheters and other medical devices. This basic procedure is commonly known as the Seldinger technique, and was first popularized during the late 1950s and 1960s.

Conventional wire guides must have sufficient flexibility and torque control for navigation through tortuous vessels and ducts. At the same time, the wire guide must have a certain amount of rigidity to pass through lesions, straighten extremely tortuous vessels, and support medical catheter devices that are subsequently introduced over the wire guide. Wire guides are therefore subject to potentially conflicting requirements. For example, more flexible, smaller diameter wire guides are preferable for navigation of extremely tortuous vessels and ducts. However, in some situations the tip of the wire guide may prolapse away from the site to which access is trying to be gained, or when encountering obstructions within the vessel or duct. On the other hand, stiffer, larger diameter wire guides generally do not have sufficient flexibility to navigate extremely tortuous vessels or ducts. Larger diameter wire guides may also be too large to be used to introduce smaller catheter devices having small wire guide lumens. In addition, certain portions of the vessel or duct may require a stiffer, larger diameter wire guide, whereas other portions of the vessel or duct may require a more flexible, smaller diameter wire guide. As a consequence, the user may need to introduce multiple wire guides having different diameters and properties.

In an exemplary medical procedure, the user begins with a larger diameter, stiffer wire guide to gain access through the larger, less tortuous vessel or duct. As the vessel or duct becomes smaller and more tortuous, the user may need to replace the larger wire guide with a more flexible, smaller diameter wire guide to gain access therethrough. The wire guide exchange may be accomplished by passing a catheter over the first wire guide until the distal end of the catheter is near the distal end of the wire guide. The wire guide is then withdrawn and removed from the catheter. Once the first wire guide is removed, the catheter can then be utilized to introduce and advance the second wire guide through the wire guide lumen of the catheter. The catheter provides the necessary support for the second wire guide as it is being advanced there through. The second wire guide can then be extended beyond the distal end of the catheter to gain access to the next section of the vessel or duct. If an obstruction or tortuous pathway is encountered that can not be passed by the second wire guide, then the second wire guide may need to be replaced with a third wire guide.

The need to exchange wire guides during the medical procedure adds to the complexity and duration of the procedure. In addition, exchanging one wire guide for another increases the likelihood of contamination to the patient and to those performing the medical procedure. Accordingly, there is a need to provide a wire guide that can be altered during the medical procedure to reduce or increase its stiffness, cross-sectional shape or diameter.

In another exemplary procedure, the user may need to introduce a second wire guide along side the first wire guide. In particular, the user may need to simultaneously gain and maintain access to each leg of a bifurcated duct. For example, the user may need to introduce a first wire guide into the biliary duct and a second wire guide into the pancreatic duct. In such a procedure, the user will introduce the first wire guide into the biliary duct using the conventional manner. The user will then attempt to introduce the second wire guide into the pancreatic duct by first threading it along side of the first wire guide and into the biliary duct, and then subsequently into the pancreatic duct. The procedure is time consuming and difficult, particularly since the biliary duct may be partially obstructed by the presence of the first wire guide. Accordingly, there is a need to provide a wire guide that can be separated during the medical procedure into two or more separate wire guide members, wherein each of the wire guide members may be used to gain access to a different vessel or duct.

SUMMARY OF THE INVENTION

Accordingly, the present invention comprises a wire guide having a plurality of separable elongate components that may be separated or otherwise re-positioned relative to each other so as to alter the physical properties of the wire guide or to form a plurality of separate wire guide members.

According to one aspect of the invention, the wire guide comprises a plurality of separable elongate components that are longitudinally engaged with each other so as to form a composite wire guide structure having a composite configuration. The separable elongate components may be longitudinally separated from each other so as to form a plurality of separate wire guide members, each of the wire guide members having a configuration that is different from the composite configuration. In one exemplary embodiment, the composite wire guide may be separated into two individual wire guide members, each having a cross-section and stiffness that is less than the composite wire guide. The composite wire guide may be separated into individual wire guide members while disposed at least partially within a vessel or duct of the patient, or may be separated while outside patient. The individual wire guide members may then be utilized for different aspects of the medical procedure, such as the placement of an individual wire guide member in each leg of a bifurcated duct. Or alternatively, the medical procedure may commence or continue with only one of the individual wire guide members, with the other wire guide members being re-positioned or removed and discarded so as to not interfere with the procedure. A tool may also be provided to facilitate separation of the composite wire guide into individual wire guide members.

According to another aspect of the invention, the wire guide comprises a plurality of separable elongate components that may be longitudinally separated from each other so as to form a plurality of separate wire guide members. In one particular embodiment, the wire guide comprises a longitudinal score, perforation or weakness along the length thereof to facilitate separation of the wire guide into separate wire guide components. For example, the wire guide may comprise a pair of longitudinally extending score lines disposed along opposite sides thereof, the score lines permitting the wire guide to be split or peeled into two separate elongate wire guide halves. In another embodiment, the wire guide comprises a plurality of individual wire guide members that interlock with each other, either directly or through a separate interlocking core member. For example, the wire guide may comprise two elongate wire guide members, wherein the first elongate wire guide member has a female keyway disposed along the length thereof and the second elongate wire guide member has a male key disposed along the length thereof, the male key being configured to engage and interlock with the female keyway. The key and keyway configuration permits the individual elongate wire guide members to function together as a single, composite wire guide, while still allowing the individual elongate wire guide members to be separated from each other when so desired by the user. In certain embodiments, the key and keyway configuration forms a relatively weak connection between the individual elongate wire guide members that can be overcome by laterally pulling the individual elongate wire guide members away from each other. In other embodiments, the key and keyway configuration forms a relatively strong connection between the individual elongate wire guide members that resists lateral separation, and must be overcome by longitudinally sliding the individual elongate wire guide members relative to each other until they are separated. In another alternative embodiment, each of the elongate wire guide members comprises a female keyway, and a separate male key core member engages and interlocks with the female keyway of each of the elongate wire guide members and secures the elongate wire guide members together. In this alternative embodiment, the elongate wire guide members may be separated by removing the male key core member.

According to another aspect of the invention, the wire guide comprises a plurality of separable elongate components that may be longitudinally separated or re-positioned relative to each other so as to alter the physical properties of the wire guide. In one particular embodiment, the wire guide includes an outer shaft portion and a core member that is slidably disposed within the outer shaft portion. The physical properties of the wire guide may be altered by re-positioning the core member relative to the shaft portion. For example, the core portion may be partially or completely withdrawn in a proximal direction relative to the shaft portion so as to increase the flexibility of the shaft portion. Alternatively, the core portion may be advanced distally relative to the shaft portion to thereby increase the overall length of the wire guide. When in this configuration, the core portion may function as a smaller, more flexible wire guide for gaining access to a more tortuous section of the vessel or duct.

These and other advantages, as well as the invention itself, will become apparent in the details of construction and operation as more fully described below. Moreover, it should be appreciated that several aspects of the invention can be used with other types of wire guides, wire guided catheters, and other medical devices.

DESCRIPTION OF THE INVENTION

Figure 1:
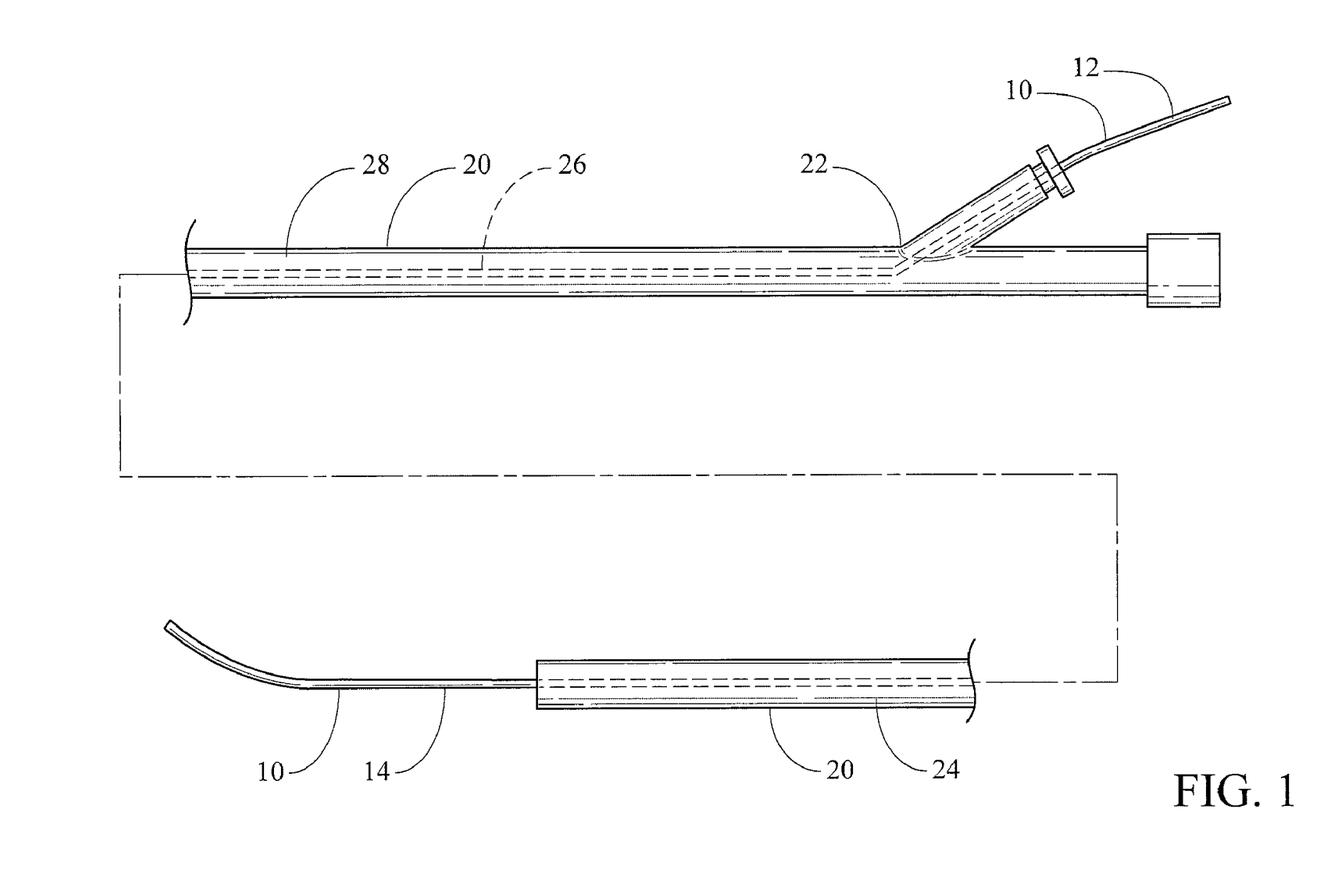
FIG. 1 is a side view of an exemplary wire guide according to the present invention disposed through an elongate medical catheter.

Turning now to FIG. 1, one embodiment of an exemplary splittable wire guide 10 according to the present invention is shown disposed through an elongate medical device or catheter 20. In the embodiment illustrated, the wire guide 10 comprises a proximal end 12 and a distal end 14. Likewise, the catheter 20 comprises a shaft 28 having a proximal end 22, a distal end 24, and a lumen 26 extending at least partially therethrough. In the embodiment illustrated, the wire guide 10 has a length that is greater than the length of the catheter lumen 26. In some embodiments, the length of the wire guide 10 may be twice as long as the length of the catheter lumen 26 to facilitate wire guide/catheter exchange procedures. As will be understood by those skilled in the art of minimally invasive medical procedures, the catheter 20 may be advanced over a wire guide 10 previously placed within the patient's body, or may be utilized to advance a wire guide 10 into the patient's body. The manner of introduction and advancement of the wire guide 10 (and catheter 20) will depend of the type and stage of medical procedure being performed.

Figure 2:
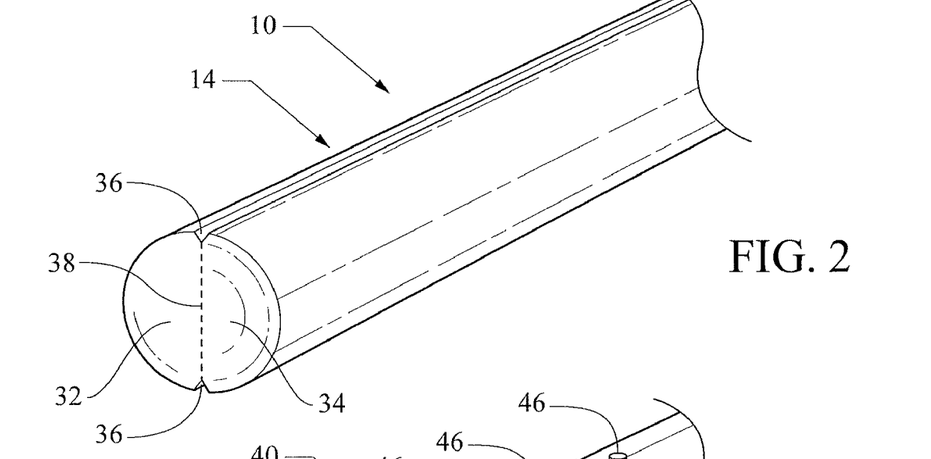
FIG. 2 illustrates a distal portion an embodiment of a wire guide comprising a longitudinal score extending along the length thereof.

Turning now to FIG. 2, the distal end 14 of a first embodiment of a wire guide 10 according to the present invention is illustrated. Wire guide 10 comprises a generally circular cross-section and is separable into two separate elongate wire guide members. More specifically, wire guide 10 comprises a first wire guide member 32 and a second wire guide member 34, each having a generally D-shaped cross-section. The interface 38 between the first and second wire guide members 32, 34, is defined by a pair of score lines 36 extending longitudinally along the length of the wire guide 10. As will be explained in greater detail below, the score lines 36 facilitate separation of the wire guide 10 into separate first and second wire guide members 32, 34. The score lines 36 can be formed by sciving, cutting, excising or otherwise removing material from opposite sides of the shaft of the wire guide 10. For example, a knife can be used to cut a longitudinally oriented V-shaped groove along opposite sides of the shaft of the wire guide 10. As will be understood by those skilled in the art, increasing the depth of the score lines 36 will reduce the effort needed to separate the wire guide 10 into separate first and second wire guide members 32, 34.

In an exemplary procedure, the wire guide 10 may be introduced into the body of a patient using conventional methods of introduction. For example, during a typical endoscopic retrograde cholangiopancreatopography (ERCP) procedure, the wire guide 10 is advanced through the accessory channel of an endoscope until the distal end 14 is positioned within the duodenum and near the papilla of Vater. The distal end 14 of the wire guide 10 is then further advanced through the sphincter of Oddi and into the bile duct. The wire guide 10 is then utilized as a guide for the advancement of a medical device such as an ERCP catheter. At this stage, if the physician desires to gain access to the pancreatic duct, then the wire guide 10 is typically withdrawn from the bile duct and redirected into the pancreatic duct. Alternatively, a second wire guide may be advanced through the endoscope and into the pancreatic duct. But as explained in the background section, introduction of a second wire guide is time consuming and may be difficult or impossible to perform. The wire guide 10 of the present invention, however, provides another alternative. The wire guide 10 may be separated into separate first and second wire guide members 32, 34, with the first wire guide member 32 being directed into the bile duct and the second wire guide member being directed into the pancreatic duct. In an exemplary procedure, the wire guide 10 is separated into two separate wire guide members 32, 34 after the distal end 14 thereof has been advanced through the sphincter of Oddi but before being advance into either the bile or pancreatic ducts. This allows the greater strength of the combined cross-section of the wire guide 10 to be utilized for the majority of the advancement procedure.

In the embodiment illustrated, first and second wire guide members 32, 34 have approximately equal cross-sectional shapes and areas. However, it should be understood that other cross-sectional shapes and/or non-equal areas can be employed. For example, first wire guide member 32 may have a larger in cross-sectional area than second wire guide member 34. This may be accomplished by shifting score lines 36 to one side of the wire guide 10, thereby offsetting interface 38 from the central axis of the wire guide 10. In such an embodiment, first and second wire guide members 32, 34 will have different dimensions and physical properties. This may be advantageous because it provides the user with essentially three different types of wire guides each having a different dimension and property—a first type comprised of the unseparated cross-section of wire guide 10, a second type comprised of the cross-section of the first wire guide member 32, and a third type comprised of the cross-section of the second wire guide member 34. The user may begin the medical procedure with the unseparated cross-section of wire guide 10 and then subsequently alter wire guide 10 to form (and utilize) one or both of the separated first and second wire guide members 32, 34 for the remaining portions of the procedure. Alternatively, the user may elect to separate wire guide 10 prior to the medical procedure and then utilize one or both of the first and second wire guide members 32, 34 at the outset of the procedure.

Figure 3:
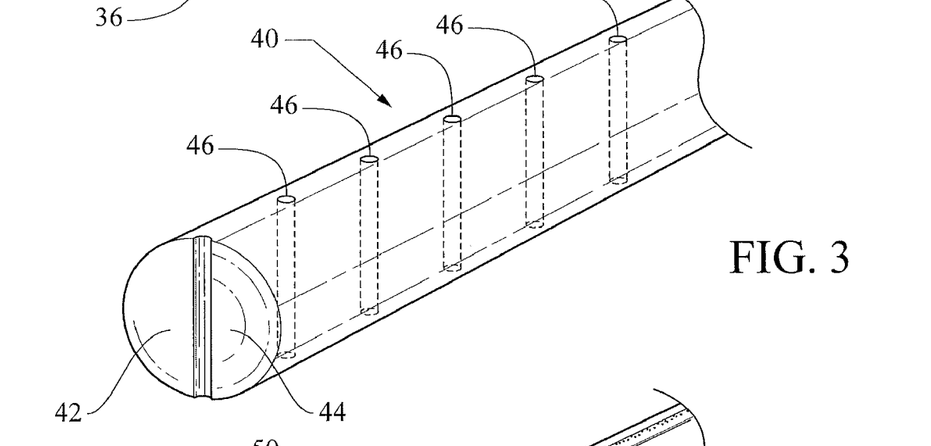
FIG. 3 illustrates a distal portion an embodiment of a wire guide comprising a perforation extending longitudinally along the length thereof.

FIG. 3 illustrates an alternative embodiment of the splittable wire guide according to the present invention. In the embodiment illustrated, the wire guide 40 comprises a first wire guide member 42 and a second wire guide member 44. The boundary between the first and second wire guide members 42, 44 is defined by a plurality of perforations 46 extending through the shaft of the wire guide 40 and spaced longitudinally along the length thereof. The perforations 46 facilitate separation of the wire guide 40 into separate first and second wire guide members 42, 44. More specifically, the perforations 46 reduce the amount of shaft material joining the first and second wire guide members 42, 44 together. The perforations 46 may be formed by several techniques known to those skilled in the art, such as drilling or laser cutting. As will also be understood by those skilled in the art, increasing the cross-section and frequency of the perforations 46 will reduce the effort needed to separate the wire guide 40 into separate first and second wire guide members 42, 44. The location of the perforations 46 may also be offset from the central axis of the wire guide 40 so as to define/form first and second wire guide members 42, 44 having different cross-sectional areas and properties.

Figure 4:
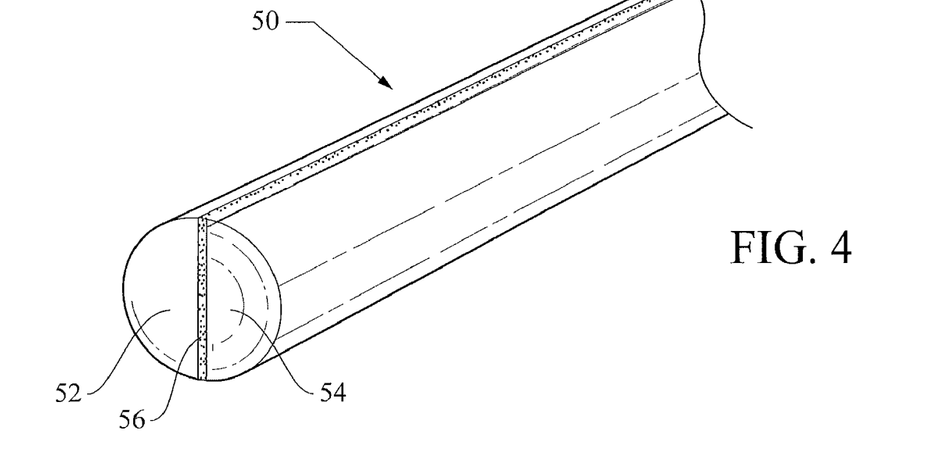
FIG. 4 illustrates a distal portion an embodiment of a wire guide comprising a weakened area extending longitudinally along the length thereof.

FIG. 4 illustrates another alternative embodiment of the splittable wire guide according to the present invention. In the embodiment illustrated, the wire guide 50 comprises a first wire guide member 52 and a second wire guide member 54. The first and second wire guide members 52, 54 are joined together by a weakened area 56 extending longitudinally through and along the shaft of the wire guide 50. The weakened area 56 facilitates separation of the wire guide 50 into separate first and second wire guide members 52, 54. The weakened area 56 may comprise an adhesive layer between the first and second wire guide members 52, 54, or may be formed of a material having a relatively weak tensile strength. As will be understood by those skilled in the art, a variety of materials may be utilized for weakened area 56. The location of the weakened area 56 may also be offset from the central axis of the wire guide 50 so as to define/form first and second wire guide members 52, 54 having different cross-sectional areas and properties. Likewise, wire guide 50 may comprise a plurality of weakened areas to facilitate separation of the wire guide 50 into more than two separate wire guide members.

In the embodiments illustrated in FIGS. 2-4, the wire guides 10, 40, 50 are preferably manufactured from a solid or uniform material. For example, the wire guides 10, 40, 50 may be manufactured from metal, which would provide the necessary rigidity and other properties suitable for medical wire guide devices. Moreover, a solid metal composition is amenable to manufacturing techniques such as sciving, cutting and drilling, thereby allowing the construction of the above-described embodiments shown in FIGS. 2-3. Other materials, such as high-density plastics or polymers, may also be suitable.

Figures 5, 6, 7:
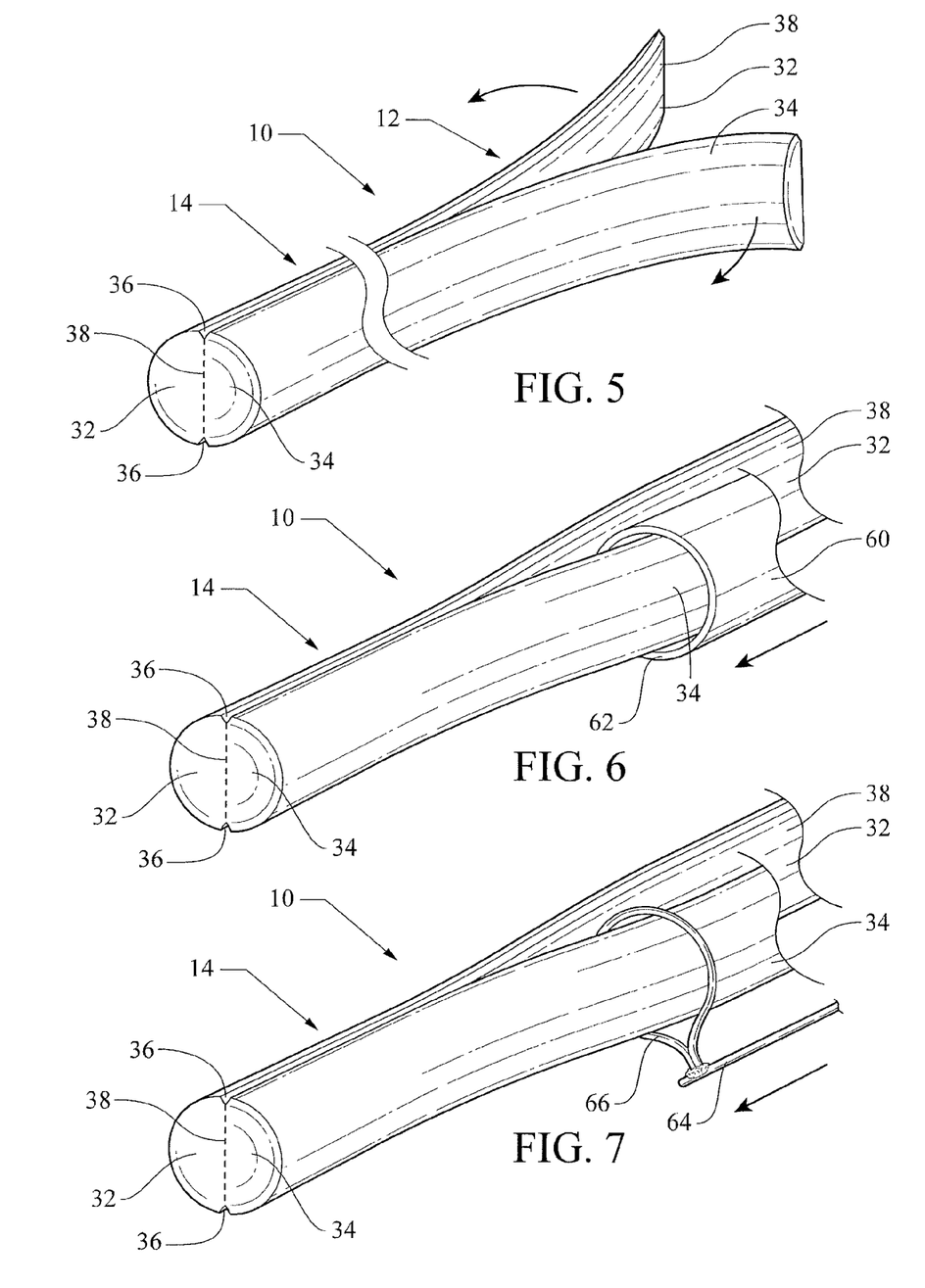
FIG. 5 illustrates the step of separating the wire guide of FIG. 2 into two separate wire guide components by pulling the components in a lateral direction.
FIG. 6 illustrates the step of separating the wire guide of FIG. 2 into two separate wire guide components by advancing an elongate sheath over one of the components.
FIG. 7 illustrates the step of separating the wire guide of FIG. 2 into two separate wire guide components by advancing a loop member over one of the components.

FIGS. 5-7 illustrate various methods and/or devices for separating the wire guide 10 of FIG. 2 into separate first and second wire guide members 32, 34. FIG. 5 illustrates the step of separating the wire guide 10 into two separate wire guide members 32, 34, by pulling the individual members in a lateral direction and away from each other. For example, and as illustrated in FIG. 5, a user may individually grasp both first and second wire guide members 32, 34 near the proximal end 12 of the wire guide 10. The user then applies a laterally directed opposing force to each of the first and second wire guide members 32, 34 that is sufficient to cause the members to separate or peel away from each other along the score lines 36 and interface 38. Application of the lateral force is continued until the first and second wire guide members 32, 34 have been completely separated from each other. Alternatively, the first and second wire guide members 32, 34 may be separated by applying a longitudinally directed force to the juncture between the members. For example, the user may grasp both wire guide members 32, 34 with one hand while using the finger of the other hand (or a tool) to split the wire guide 10 by advancing the finger (or tool) longitudinally along the interior surfaces (i.e., interface 38) of the wire guide members 32, 34.

FIG. 6 illustrates the step of separating the wire guide 10 into two separate wire guide members 32, 34 by advancing an elongate sheath 60 over one of the members. For example, and as illustrated in FIG. 6, a user may grasp first wire guide member 32 near the proximal end 12 of the wire guide 10. The user then positions sheath 60 over the proximal end of second wire guide member 34 so as to engage the juncture between wire guide members 32, 34 with the distal end 62 of the sheath 60 along interface 38. Further advancement of sheath 60 relative to wire guide 10 causes the distal end 62 of the sheath 60 to apply a force sufficient to separate the first and second wire guide members 32, 34 from each other.

FIG. 7 illustrates the step of the step of separating the wire guide 10 into two separate wire guide members 32, 34 by advancing a push rod 64 with a loop 66 attached thereto over one of the members. For example, and as illustrated in FIG. 7, a user may grasp first wire guide member 32 near the proximal end 12 of the wire guide 10. The user then positions the loop 66 over the proximal end of second wire guide member 34 so that a portion of the loop 66 engages the juncture between wire guide members 32, 34. Advancement of push rod 64 relative to wire guide 10 causes the loop 66 to apply a force sufficient to separate the first and second wire guide members 32, 34 from each other.

Figure 8:
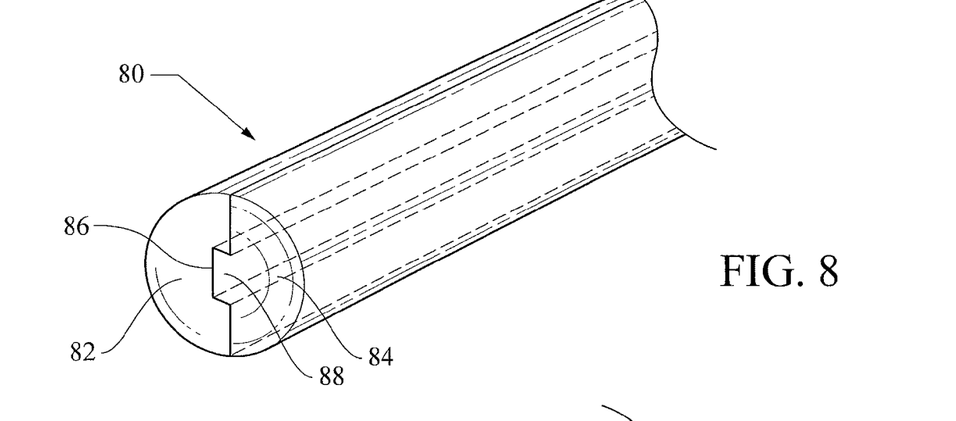
FIG. 8 illustrates a distal portion of an embodiment of a wire guide comprising a two separate wire guide components that are connected by a key and keyway structure.

FIGS. 8-13 illustrate additional alternative embodiments of the splittable wire guide according to the present invention. In each of these embodiments, the wire guide comprises a plurality of individual wire guide members that engage and/or interlock with each other. For example, FIG. 8 illustrates a wire guide 80 comprising two separable elongate wire guide members 82, 84 that are connected together via a key and keyway arrangement. In particular, the first elongate wire guide member 82 has a rectangular shaped female keyway 86 disposed longitudinally along the length thereof. The second elongate wire guide member 84 has a rectangular shaped male key 88 disposed longitudinally along the length thereof. The male key 88 is configured to engage and interlock with the female keyway 86 so as to secure wire guide members 82, 84 together. In the particular embodiment illustrated, the key 88 is sized and configured to engage with the keyway 86 with a sufficient frictional force to prevent wire guide members 82, 84 from separating from each other during ordinary use of the wire guide 80. However, the key 88 and keyway 86 are nevertheless configured to permit wire guide members 82, 84 to be separated from each other upon the application of a sufficient separating force (for example, by utilizing the separating methods described above in connection with FIGS. 5-7). The key 88 and keyway 86 may also include an adhesive layer disposed there between to increase (or decrease) the strength of the connection between wire guide members 82, 84.

Figure 9:
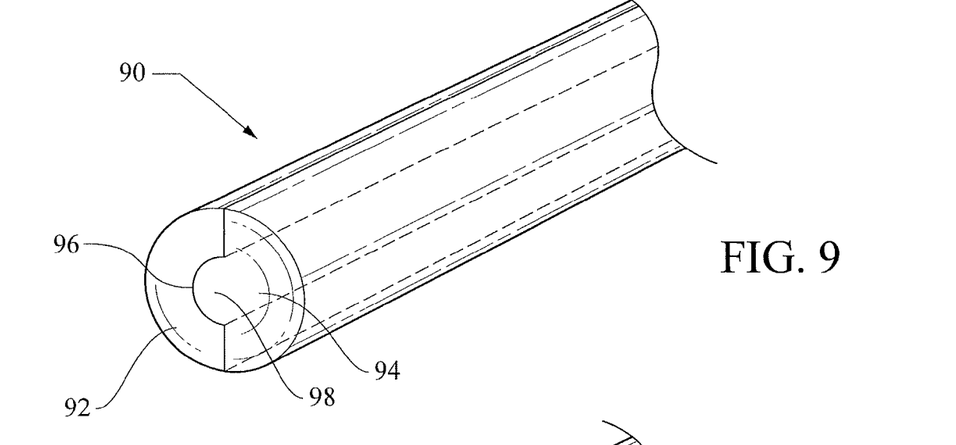
FIG. 9 illustrates a distal portion of another embodiment of a wire guide comprising a two separate wire guide components that are connected by a key and keyway structure.
Figure 10:
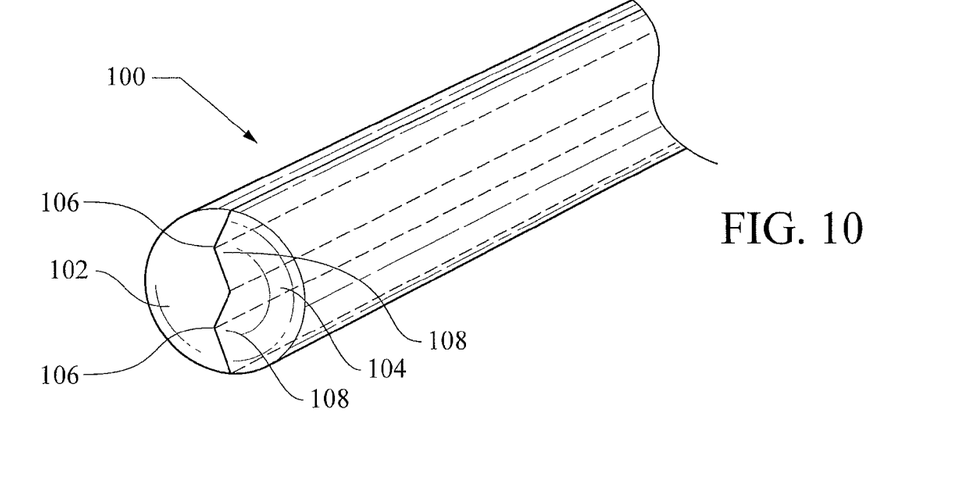
FIG. 10 illustrates a distal portion of another embodiment of a wire guide comprising a two separate wire guide components that are connected by a key and keyway structure.

FIGS. 9-10 illustrate alternative embodiments of splittable wire guides similar to the embodiment of FIG. 8, but having differently shaped keys and keyways that provide a relatively weaker mechanical connection there between. The wire guide 90 illustrated in FIG. 9 comprises a two separable elongate wire guide members 92, 94 that are connected together via a key and keyway arrangement having a semi-circular shape. More specifically, first wire guide member 92 comprises a keyway 96 having a generally concave shape, and second wire guide member 94 comprises a key 98 having a generally convex shape. The wire guide 100 illustrated in FIG. 10 comprises a two separable elongate wire guide members 102, 104 that are connected together via a plurality of key and keyway arrangements, each generally triangular in shape. More specifically, first wire guide member 102 comprises a pair of keyways 106 each having a triangular indentation, and second wire guide member 104 comprises a pair of keys 108 each having a triangular protrusion. Of course, it should be appreciated that the area between the pair of key and keyway arrangements could similarly be construed as forming an additional key and keyway arrangement.

The semi-circular and triangular shape of the key and keyway arrangements of the embodiments illustrated in FIGS. 9-10 provide a mechanical connection between the separate wire guide members that is generally weaker than the key and keyway arrangement of the embodiment illustrated in FIG. 8. In other words, the embodiments illustrated in FIGS. 9-10 will generally require a smaller separation force to separate the wire guide 90, 100 into individual wire guide members. However, because the semi-circular and triangular key and keyway arrangements may not be capable of generating a sufficient frictional force to prevent the individual wire guide members from separating from each other during ordinary use of the wire guide 90, 100, it may be necessary to utilize an adhesive between the key and keyway.

Figure 11:
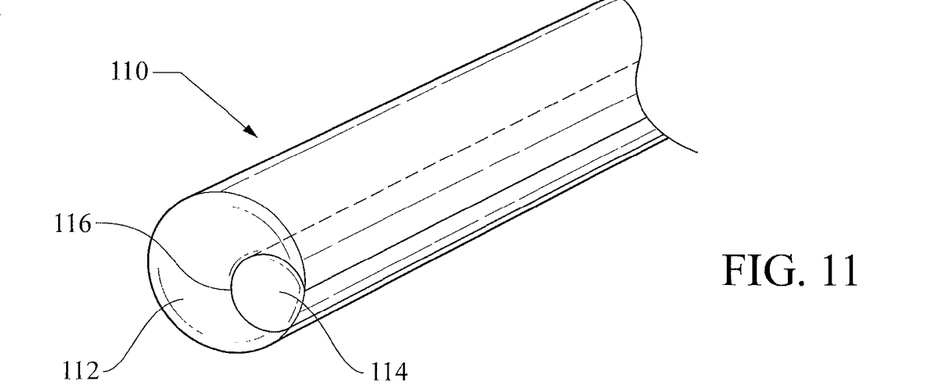
FIG. 11 illustrates a distal portion of another embodiment of a wire guide comprising a two separate wire guide components that are connected by a key and keyway structure.
Figure 12:
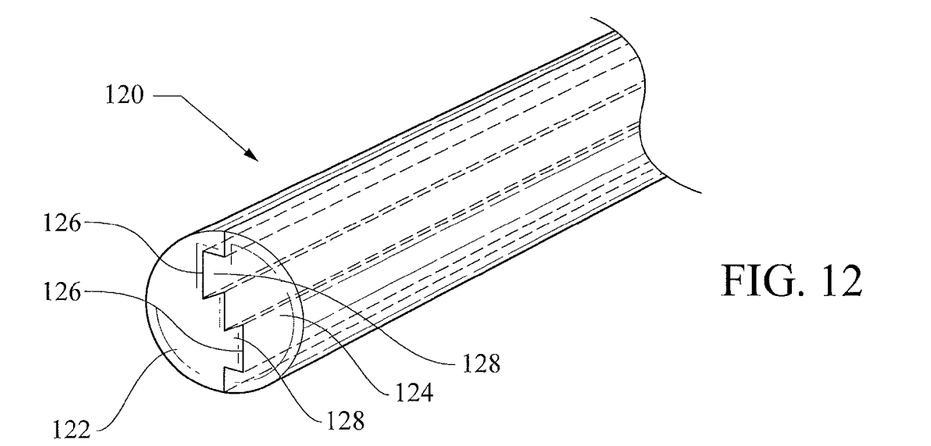
FIG. 12 illustrates a distal portion of another embodiment of a wire guide comprising a two separate wire guide components that are connected by a key and keyway structure.

FIGS. 11-12 illustrate further alternative embodiments of splittable wire guides similar to the embodiment of FIG. 8, but having differently shaped keys and keyways that provide a relatively stronger mechanical connection there between. The wire guide 110 illustrated in FIG. 11 comprises a two separable elongate wire guide members 112, 114 that are connected together via a key and keyway arrangement having a semi-circular shape. More specifically, first wire guide member 112 comprises a keyway 116 having a generally semi-circular shape, and second wire guide member 114 comprises a circular outer shape that is configured to fit within the keyway 116. In other words, the key is formed by the outer shape of the second wire guide member 114 and not by a separate structure. In addition, and as illustrated in FIG. 11 the keyway 116 is configured to encompass a majority of the perimeter of the second wire guide member 114. Thus, to laterally remove the second wire guide member 114 from the keyway 116 of the first wire guide member 112, the second wire guide member 114 and/or the keyway 116 of the first wire guide member must comprise a material that is sufficiently flexible to permit deformation of one or both of these structures. On the other hand, the second wire guide member 114 and/or the keyway 116 of the first wire guide member may comprise a material that is relatively inflexible and resists deformation if it is desired to inhibit or prevent lateral separation of these components.

The wire guide 120 illustrated in FIG. 12 comprises a two separable elongate wire guide members 122, 124 that are connected together via a pair of key and keyway arrangements each having a dove-tail shape. More specifically, first wire guide member 122 comprises a keyway 126 having a dove-tail shape, and further comprises a key 128 having a pin shape. The second wire guide member 124 likewise comprises a keyway 126 having a dove-tail shape, and further comprises a key 125 having a pin shape. Each pin shaped key 128 of one wire guide member is configured to fit within the respective dove-tail shaped keyway 126 of the other wire guide member. Similar to the embodiment of FIG. 11, wire guide members 122, 124 must comprise a material that is sufficiently flexible to permit deformation of one or both of the keyway 126 and key 128 to permit lateral separation of wire guide members 122, 124.

The embodiments of the splittable wires illustrated in FIGS. 11-12 also permit longitudinal displacement of one wire guide member relative to the other. For example, and with respect to the embodiment illustrated in FIG. 11, the first wire guide member 112 may be retracted proximally (or advanced distally) relative to the second wire guide member 114. Likewise, and with respect to the embodiment illustrated in FIG. 12, the first wire guide member 122 may be retracted proximally (or advanced distally) relative to the second wire guide member 124. Retraction of the first wire guide member 112, 122 relative to the second wire guide member 114, 124 may be advantageous when it is necessary or desirable to continue the medical procedure utilizing a wire guide having a reduced cross-section of increased flexibility. For example, a user may elect to begin the medical procedure using a composite wire guide 110 having a relatively large cross-section and high degree of stiffness. However, at some point during the medical procedure, the user may find it necessary or desirable to continue the procedure using only second wire guide member 114, which has a smaller cross-section and is relatively more flexible than composite wire guide 110. To accomplish this, the user may retract the first wire guide member 112 in a proximal direction, either partially or fully, relative to the second wire guide member 114. The user may then continue the medical procedure using just the second wire guide member 114. If at some point further during the medical procedure the user finds it once again necessary or desirable to utilize a larger/stiffer wire guide, then the user may re-couple (if previously separated) and advance the first wire guide member 112 relative to the second wire guide member 114 to re-form the composite wire guide 110. The embodiment of FIG. 12 may likewise be used to perform the exemplary procedure described above.

Figure 13:
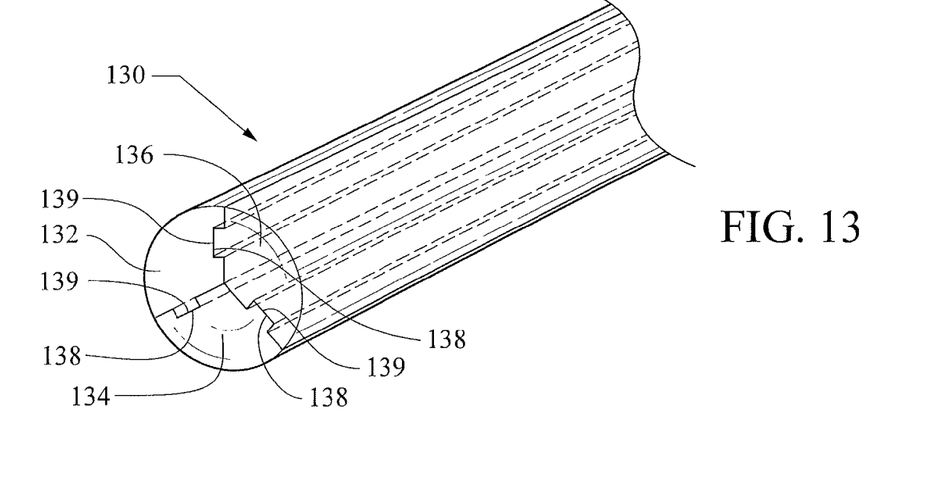
FIG. 13 illustrates a distal portion of another embodiment of a wire guide comprising a three separate wire guide components that are connected by a key and keyway structure.

FIG. 13 illustrates a further alternative embodiment of a splittable wire guide similar to the embodiment of FIG. 8, but more than two separable wire guide members. The wire guide 130 illustrated in FIG. 13 comprises a three separable elongate wire guide members 132, 134, 136 that are connected together via a key and keyway arrangement 138 having a rectangular shape. More specifically, each of the wire guide members 132, 134, 136 comprises both a key 138 and a keyway 139, wherein the key 138 of one wire guide member is configured to fit within the respective keyway 139 of one of the other wire guide members. Although the wire guide 130 of this embodiment comprises a three equally sized separable elongate wire guide members, it should be understood that the wire guide 130 may comprise any practical number of wire guide members having varying shapes and sizes.

Figure 14:
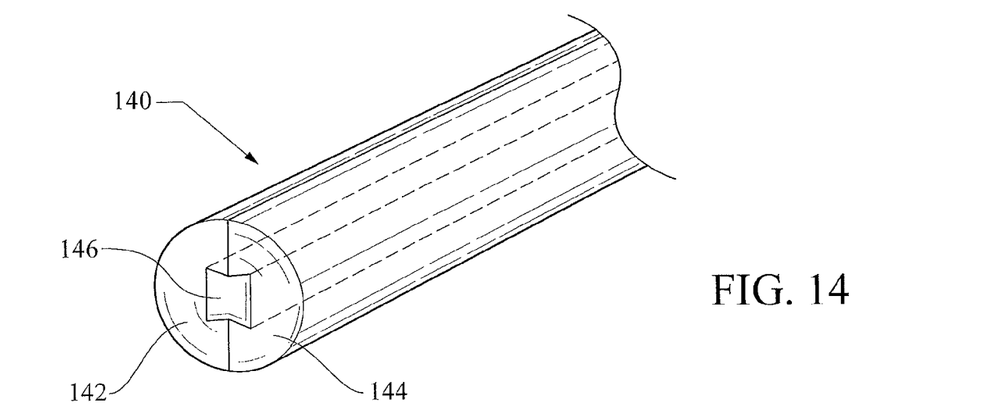
FIG. 14 illustrates a distal portion of another embodiment of a wire guide comprising a two separate wire guide components that are connected by a separate core member.
Figure 15:
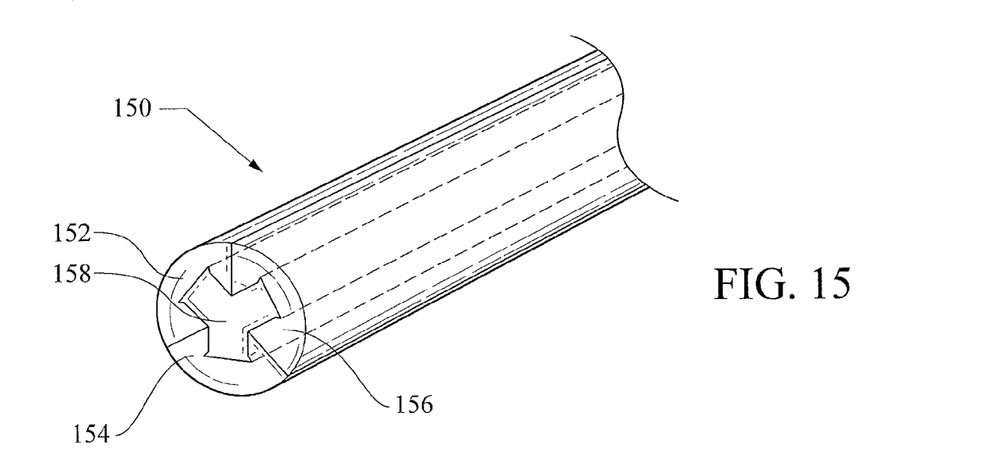
FIG. 15 illustrates a distal portion of another embodiment of a wire guide comprising a three separate wire guide components that are connected by a separate core member.
Figure 16:
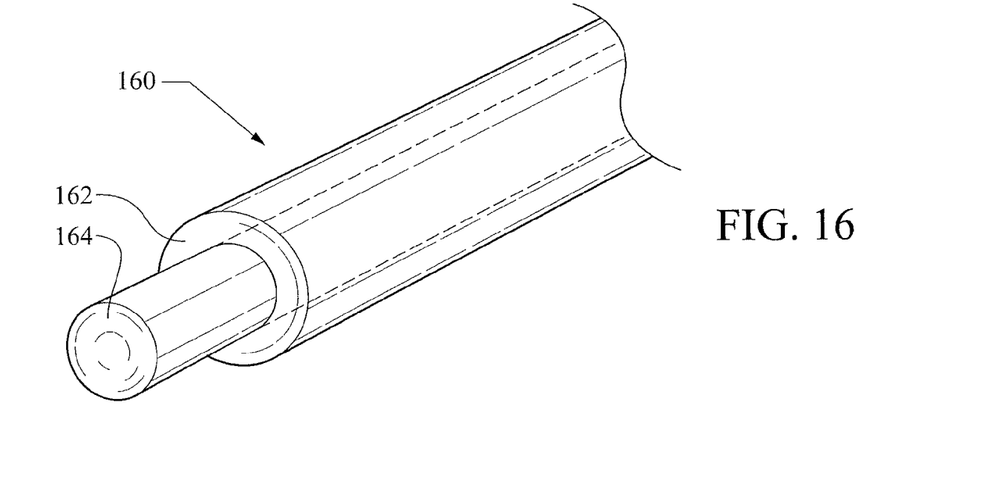
FIG. 16 illustrates a distal portion of another embodiment of a wire guide comprising a two separate wire guide components that are connected by a key and keyway structure, wherein the one of the wire guide components has been advanced relative to the other.

FIGS. 14-16 illustrate additional alternative embodiments of the splittable wire guide according to the present invention. In each of these embodiments, the wire guide comprises a plurality of individual wire guide members that are connected together via a separate core member. For example, FIG. 14 illustrates a wire guide 140 comprising two separable elongate wire guide members 142, 144 that are connected together via a separate core member 146. The core member 146 comprises a double pin shape, wherein one pin is configured to engage a dove-tail shaped keyway in the first wire guide member 142, and the other pin is configured to engage a dove-tail shaped keyway in the second wire guide member 144. In the particular embodiment illustrated, the core member 146 is sized and configured to engage with the with first and second wire guide members 142, 144 with a sufficient mechanical and/or frictional force to prevent wire guide members 142, 144 from separating from each other (and core member 146) during ordinary use of the wire guide 140. More specifically, these components comprise a material that is relatively inflexible and resists deformation so as to inhibit or prevent lateral separation of these components from each other. Instead, first wire guide member 142 is separated from second wire guide member 144 by longitudinally removing core member 146 from there between. Alternatively, the core member 146 and or first and second wire guide members 142, 144 may comprise a material that is sufficiently flexible to permit deformation of one or more of these structures if lateral separation of these components is desirable. In other words, a more flexible material can be utilized to permit the wire guide 140 to be separated by laterally peeling the individual components apart from each other.

The wire guide 150 illustrated in FIG. 15 is similar to the wire guide 140 illustrated in FIG. 14. However, the wire guide 150 of FIG. 15 comprises more than two separable wire guide members. In particular, wire guide 150 comprises a first wire guide member 152, a second wire guide member 154, and a third wire guide member 156, which are held together by core member 158. Removal of core member 158 allows wire guide 150 to be separated into three individual wire guide members 152, 154, 156.

The wire guide 160 illustrated in FIG. 16 is similar to the wire guide 140 illustrated in FIG. 14. However, the wire guide 160 of FIG. 16 comprises a second wire guide member 164 that functions as a core member. In particular, the second wire guide member 164 is movably disposed inside of the first wire guide member 162. The first wire guide member 162 may be retracted proximally, or advanced distally, relative to the second wire guide member 164 to separate these components from each other. Retraction of the second wire guide member 164 relative to the first wire guide member 162, either partially or fully, may be advantageous when it is necessary or desirable to increase the flexibility of the first wire guide member 162 without reducing its overall diameter. Similarly, retraction of the first wire guide member 162 relative to the second wire guide member 164 may be advantageous when it is necessary or desirable to continue the medical procedure utilizing a wire guide having both an increased flexibility and reduced diameter. For example, a user may elect to begin the medical procedure using a composite wire guide 160 having a relatively large cross-section and high degree of stiffness. However, at some point during the medical procedure, the user may find it necessary or desirable to continue the procedure using only the second wire guide member 164. To accomplish this, the user may retract the first wire guide member 162 in a proximal direction, either partially or fully, relative to the second wire guide member 164. The user may then continue the medical procedure using just the second wire guide member 164. If at some point further during the medical procedure the user finds it once again necessary or desirable to utilize a larger/stiffer wire guide, then the user may re-couple (if previously separated) and advance the first wire guide member 162 relative to the second wire guide member 164 to re-form the composite wire guide 160.

In another exemplary procedure, the user may elect to begin the medical procedure using a composite wire guide 160 having a relatively large cross-section and high degree of stiffness. However, at some point during the medical procedure, the user may find it necessary or desirable to continue the procedure using only the first wire guide member 162, for example, when it is desired to utilize the interior lumen of the first wire guide member 162 for delivery of a fluid such as contrast. To accomplish this, the user may retract the second wire guide member 164 in a proximal direction relative to the first wire guide member 162. The user may then utilize the lumen formed in the first wire guide member 162 by the removal of the second wire guide member 164. If at some point further during the medical procedure the user finds it once again necessary or desirable to utilize a solid wire guide, then the user may re-insert and advance the second wire guide member 164 into the first wire guide member 162 so as to re-form the composite wire guide 160.

The splittable wire guide of the present invention, as well as the individual components thereof, may be made of any suitable material such as PEEK, polyvinyl chloride (PVC), polyimide, polyimide reinforced with a stainless steel braid, polyurethane, nylon, metal tubing such as nitinol or stainless steel, and the like. The individual components, such as the individual wire guide members (and core members) described above may also be formed as a coil or a solid-core wire guide member. In certain embodiments, a substantial portion of the guide wire member is formed from nylon tubing while the distal portion is formed from polyimide. In addition, portions or the splittable wire guide, as well as the individual components thereof, may include barium sulfate or some other agent or marker to provide radiopacity. Radiopaque materials enable the user, with the aid of a fluoroscope, to determine the position of the splittable wire guide and wire guide members while disposed within the body lumen of the patient.

While there have been described what are presently believed to be the preferred embodiments of the invention, those skilled in the art will realize that changes and modifications may be made thereto without departing from the spirit of the invention. It is to be understood that the invention can be carried out by specifically different equipment and devices, and that various modifications, both as to the equipment details and operating procedures, can be accomplished without departing from the scope of the invention itself.

The invention claimed is:

1. A splittable wire guide configured for introduction into a mammalian patient comprising:
a first wire guide member having a first proximal end, a first distal end, and an elongate shaft comprising a length extending from the first proximal end to the first distal end; and
a second wire guide member having a second proximal end, a second distal end, and an elongate shaft comprising a length extending from the second proximal end to the second distal end,
wherein the shaft of the first wire guide member is removably and slidably coupled to the shaft of the second wire guide member along the entire length of both shafts such that the shaft of the first wire guide member and the shaft of the second wire guide member each form at least a portion of a circumferential exterior surface of the splittable wire guide;
wherein the shaft of the first wire guide member is longitudinally movable relative to the shaft of the second wire guide member while coupled thereto; and
wherein at least one of the first wire guide member and the second wire guide members is configured for slidable movement through a lumen of an elongate medical device.

2. The splittable wire guide according to claim 1, wherein the shaft of the first wire guide member is laterally separable from the shaft of the second wire guide member.

3. The splittable wire guide according to claim 2, wherein the shaft of the first wire guide member is laterally separable from the shaft of the second wire guide member via the application of laterally directed opposing forces to the first and second wire guide members.

4. The splittable wire guide according to claim 3 further comprising a separating member, wherein the separating member is configured to apply the laterally directed opposing forces to the first and second wire guide members.

5. The splittable wire guide according to claim 4, wherein the separating member comprises an elongate catheter having a lumen extending at least partially therethrough, one of the first and second wire guide members being disposed through the lumen.

6. The splittable wire guide according to claim 2, wherein one of the first and second wire guide members comprises a female keyway extending along the entire length of the shaft and the other comprises a male key extending along the entire length of the shaft, the male key being removably and slidably engaged with the female keyway.

7. The splittable wire guide according to claim 1, wherein one of the first and second wire guide members comprises a female keyway extending along the entire length of the shaft and the other comprises a male key extending along the entire length of the shaft, the male key being longitudinally movable along the female keyway.

8. The splittable wire guide according to claim 1, wherein the shaft of the first wire guide member comprises a cross-sectional area that is different from the cross-sectional area of the shaft of the second wire guide member.

9. The splittable wire guide according to claim 1, wherein the shaft of the first wire guide member comprises a stiffness that is different from the stiffness of the shaft of the second wire guide member.

10. The splittable wire guide according to claim 1 further comprising a third wire guide member having a third proximal end, a third distal end, and an elongate shaft comprising a length extending from the third proximal end to the third distal end, wherein the shaft of the third wire guide member is removably and slidably coupled to at least one of the shaft of the first wire guide member and the shaft of the second wire guide member along the entire length of the both shafts.

11. The splittable wire guide according to claim 1, wherein at least one of the first wire guide member and the second wire guide members is slidably disposed through a lumen of an elongate medical device.

12. The splittable wire guide according to claim 11, wherein the elongate medical device comprises a medical catheter.

13. A method of performing a medical procedure comprising the steps of:
providing a splittable wire guide comprising a circumferential exterior surface, a first wire guide member and a second wire guide member, the first wire guide member and the second wire guide member each forming at least a portion of the exterior surface, each of the first and second wire guide members having an elongate shaft extending between a proximal end and a distal end, the shaft of the first wire guide member being removably and slidably coupled to the shaft of the second wire guide member along the entire length thereof such that the shafts are coupled together at all locations between the proximal and distal ends;

introducing the splittable wire guide into the bodily lumen of a patient;

at least partially separating the first wire guide member from the second wire guide member while within the bodily lumen of the patient; and advancing the first wire guide member further into the bodily lumen of the patient by advancing the distal end of the first wire guide beyond the distal end of the second wire guide while maintaining at least a partial coupling of the first wire guide member to the second wire guide member.

14. The method of claim 13 further comprising the step of removing the second wire guide member from the bodily lumen of the patient.

15. The method of claim 13, wherein the step of at least partially separating the first wire guide member from the second wire guide member while within the bodily lumen of the patient comprises laterally separating the shaft of the first wire guide member from the shaft of the second wire guide member along a portion thereof.

16. The method of claim 15, wherein a separating member is utilized to at least partially separate the first wire guide member from the second wire guide member while within the bodily lumen of the patient.

17. The method of claim 16, wherein the separating member comprises a catheter that is advanced over the shaft of one of the first and second wire guide members.

18. The method of claim 13, further comprising the step of advancing an elongate medical device over the first wire guide member, the elongate medical device comprising a lumen extending at least partially therethrough, the first wire guide member being slidably disposed through the lumen during advancement of the elongate medical device.

19. A splittable wire guide configured for introduction into a mammalian patient comprising:
    a first wire guide member having an elongate shaft; and
    a second wire guide member having an elongate shaft,
    wherein the shaft of the first wire guide member is laterally separable from the shaft of the second wire guide member;
    wherein the shaft of the first wire guide member is longitudinally slidable relative to the shaft of the second wire guide member while coupled thereto;
    wherein at least one of the first wire guide member and the second wire guide members is configured for slidable movement through a lumen of an elongate medical device; and
    wherein each of the first and second wire guide members comprises a female keyway that is removably engaged with a core member, the core member being disposed within the first and second wire guide members.

20. The splittable wire guide according to claim 19, wherein the core member is longitudinally movable relative to the shafts of the first and second wire guide members.

21. A splittable wire guide configured for introduction into a mammalian patient comprising:
    a first wire guide member having an elongate shaft;
    a second wire guide member having an elongate shaft; and
    a third wire guide member having an elongate shaft,
    wherein the shaft of the first wire guide member is removably coupled to the shaft of the second wire guide member;
    wherein the shaft of the third wire guide member is removably coupled to at least one of the shaft of the first wire guide member and the shaft of the second wire guide member;
    wherein the shaft of the first wire guide member is longitudinally slidable relative to the shaft of the second wire guide member while coupled thereto;
    wherein each of the first, second and third wire guide members comprises a female keyway that is removably engaged with a core member, the core member being disposed within the first, second and third wire guide members; and
    wherein at least one of the first wire guide member and the second wire guide members is configured for slidable movement through a lumen of an elongate medical device.

22. The splittable wire guide according to claim 21, wherein the core member is longitudinally movable relative to the shafts of the first, second and third wire guide members.

* * * * *